(12) United States Patent
Ross (10) Patent No.: US 8,513,022 B2
(45) Date of Patent: Aug. 20, 2013

(54) ANALYTICAL METHOD AND APPARATUS (75) Inventor: Fraser John Ross, Ballajura (AU)

(73) Assignee: Cyantific Instruments Pty Ltd, Melbourne (AU)

( * ) Notice: Subject to any disclaimer, the term of this patent is extended or adjusted under 35 U.S.C. 154(b) by 36 days.

(21) Appl. No.: 12/808,634

(22) PCT Filed: Dec. 18, 2008

(86) PCT No.: PCT/AU2008/001864
§ 371 (c)(1),
(2), (4) Date: Aug. 25, 2010

(87) PCT Pub. No.: WO2009/079689
PCT Pub. Date: Jul. 2, 2009

(65) Prior Publication Data
US 2011/0039347 A1 Feb. 17, 2011

(30) Foreign Application Priority Data

Dec. 20, 2007 (AU) ................... 2007906997

(51) Int. Cl.
*G01N 30/08* (2006.01)
*G01N 33/00* (2006.01)
*G01N 1/40* (2006.01)
*G01N 21/01* (2006.01)
*G01N 30/34* (2006.01)

(52) U.S. Cl.
USPC ......... 436/109; 422/68.1; 422/81; 422/82.09; 422/83; 422/88; 422/91; 436/106; 436/111; 436/112; 436/113; 436/129; 436/164; 436/167; 436/174; 436/177; 436/178; 436/181

(58) Field of Classification Search
USPC ................. 436/106, 109, 164, 167, 174, 181, 436/109.111–113, 129, 177–178; 422/62, 422/68.1, 80–81, 82.05, 82.09, 83, 88, 91
See application file for complete search history.

(56) References Cited

U.S. PATENT DOCUMENTS 2,382,381 A * 8/1945 Calvert et al. ................. 436/120
3,394,080 A * 7/1968 Hoffmann et al. ............ 210/746
3,708,265 A 1/1973 Lyshkow (Continued)

FOREIGN PATENT DOCUMENTS

GB 2358817 8/2001

OTHER PUBLICATIONS

Ludzack F. J. et al, Analytical Chemistry 1954, 26, 1784-1792.*
Goulden, P. D. et al, Analytical Chemistry 1972, 44, 1845-1849.*

(Continued)

*Primary Examiner* — Arlen Soderquist
(74) *Attorney, Agent, or Firm* — Swanson & Bratschun, L.L.C.

(57) ABSTRACT

A method for determining the amount of a chemical species in a sample, in particular the amount of weak acid dissociable cyanide or total cyanide in a sample, and an apparatus for performing said method. The method comprises the steps of: i) treating the sample to liberate the chemical species into a gaseous stream; ii) directing the gaseous stream to a scrubber; iii) absorbing the chemical species into a scrubber solution; and iv) determining the amount of chemical species absorbed into the scrubber solution, wherein any remaining chemical species not absorbed into the scrubber solution is directed or recirculated to the scrubber in the gaseous stream and step iii) is repeated to increase absorption of the chemical species prior to performing step iv).

26 Claims, 3 Drawing Sheets

(56) References Cited

U.S. PATENT DOCUMENTS

| | | | | |
|---|---|---|---|---|
| 3,716,334 | A | * | 2/1973 | Pont .............................. 205/780 |
| 3,920,396 | A | * | 11/1975 | Schuy ............................ 436/68 |
| 3,920,419 | A | * | 11/1975 | Schroeder et al. .................. 95/9 |
| 3,929,411 | A | * | 12/1975 | Takano et al. .................. 436/180 |
| 4,081,345 | A | * | 3/1978 | Tolg et al. ..................... 204/405 |
| 4,140,586 | A | * | 2/1979 | Kwasnoski et al. ............ 203/47 |
| 4,191,541 | A | | 3/1980 | Jenkins |
| 4,230,665 | A | * | 10/1980 | Huber ............................ 422/64 |
| 4,268,478 | A | * | 5/1981 | Huber ....................... 422/82.09 |
| 4,299,593 | A | * | 11/1981 | Dopp ............................ 436/109 |
| 4,321,059 | A | * | 3/1982 | Voigt et al. ..................... 436/109 |
| 4,335,438 | A | * | 6/1982 | Smolen ........................... 702/19 |
| 4,752,400 | A | * | 6/1988 | Pearson ......................... 210/718 |
| 4,804,631 | A | * | 2/1989 | Lue-Hing et al. ............. 436/109 |
| 4,871,681 | A | * | 10/1989 | Bilger et al. .................. 436/109 |
| 5,218,856 | A | * | 6/1993 | Doyle ............................ 73/19.1 |
| 5,368,754 | A | * | 11/1994 | Von Klock et al. ............ 210/806 |
| 5,389,126 | A | * | 2/1995 | Baker et al. ........................ 95/45 |
| 5,965,450 | A | * | 10/1999 | Kelada ........................... 436/109 |
| 7,186,379 | B2 | * | 3/2007 | Rosentreter et al. ........ 422/82.01 |
| 7,749,468 | B2 | * | 7/2010 | Halalay .......................... 422/235 |
| 2002/0151082 | A1 | * | 10/2002 | Rosentreter et al. .......... 436/109 |
| 2005/0191237 | A1 | * | 9/2005 | Selinger et al. ............ 423/658.2 |

OTHER PUBLICATIONS

Broderius, S. J. et al, Analytical Chemistry 1977, 49, 424-428.*
Broderius, S. J., Analytical Chemistry 1981, 53, 1472-1477.*
Sebroski, J. R. et al, Environmental Science and Technology 1997, 31, 52-57.*
Zheng, A. et al, Environmental Science and Technology 2003, 37, 107-115.*
Gonen, N. et al, Journal of Hazardous Materials 2004, B113, 231-236.*
Chou, P.-Y. et al, Journal of Agricultural and Food Chemistry 2006, 54, 1551-1556.*
Hassan, S. S. M. et al, Talanta 2007, 71, 1088-1095.*
Bark, L. S. et al, Analyst 1963, 88, 751-760.*
Shanahan, R., Journal of Forensic Science 1973, 18, 25-30.*
Fleming, S. W. et al, "On-Line Analyzer for Chlorocarbons in Wastewater" in Pollution Prevention in Industrial Processes, Chapter 6, ACS Symposium Series, Breen, J. et al. ed., 1992, vol. 508, pp. 48-61.*
Lesage, S., Journal of Chromatography 1993, 642, 65-74.*
Kolodsick, K. et al, Analytica Chimica Acta 1995, 313, 75-82.*
Aguilar, M. et al, Fresenius Journal of Analytical Chemistry 1999, 363, 121-123.*
Method 9010C "Total and Amenable Cyanide: Distillation" Revision 3, Nov. 2004, 10 pages.*
Vapur, H. et al, Hydrometallurgy 2005, 77, 279-286.*
Lv, J. et al, Forensic Science International 2005, 148, 15-19.*
Vapur, H. et al, Minerals Engineering 2007, 20, 729-737.*
Avedesian, M. M. et al, Canadian Journal of Chemical Engineering 1983, 61, 801-806.*
Engineeringnews.co.za (Nov. 3, 2006) "Mintek-developed instrument measures WAD cyanide on line"; Website [Online] Available Web Site: http://www.engineeringnews.co.za/print-version/mintekdeveloped-instrument-measures-wad-cyanide-on-line-2006-11-03; Last Update: Nov. 18, 2010; Accessed on Nov. 18, 2010.
OI Analytical, (May 8, 2007) "CNSolution™ Automated Cyanide Analyzer"; Available Web Site: http://www.oico.com/default.aspx?id=product&productID=94; Last update: Nov. 18, 2010; Accessed on: Nov. 18, 2010.
Process Analytical Systems, (Jan. 20, 2005) "WAD 1000 On-Line WAD Cyanide Analyser"; Available Web Site: http://www.process-anatytical.co.za/prod05.htm; Last update: Nov. 27, 2008; Accessed on: Nov. 18, 2010.
CyanideCode.org (May 3, 2006) Cyanide Facts: Sampling and Analysis of Cyanide in Gold Mining Operations; Website [Online] Available Web Site: http://www.cyanidecode.org/cyanide_sampling.php; Last Update: Feb. 2, 2007; Accessed on Aug. 9, 2010.
ICM Code (Sep. 2006) International Cyanide Management Institute, The International Cyanide Management Code.

\* cited by examiner

ANALYTICAL METHOD AND APPARATUS

RELATED APPLICATIONS

This application is a 35 U.S.C. §371 national phase application of PCT/AU2008/001864 (WO 2009/079689), filed on Dec. 18, 2008, entitled "Analytical Method and Apparatus", which application claims priority to Australian Application Serial No. 2007906997, filed Dec. 20, 2007, which is incorporated herein by reference in its entirety.

FIELD OF THE INVENTION

The present invention relates to a method and apparatus for the automated measurement of the amount of a chemical species in solution. The apparatus and method of the present invention are particularly suited to the automated measurement of the amount of Weak Acid Dissociable (WAD) and/or total cyanide in solution.

BACKGROUND

To date, the determination of the concentration of cyanide in solution has been largely limited to manual or semi-automated techniques due to the handling requirements of cyanide solutions. In particular, sample preparation prior to determination by silver nitrate titration has been largely limited to manual techniques due to the toxicity of HCN gas and the requirement to conduct sample preparation in a controlled environment. Nevertheless, some fully automated instruments have been developed for the analysis of free cyanide involving potentiometric determination.

"Free" cyanide analysis involves the determination of the amount of $CN^-$ and HCN species in a sample. In contrast, Weak Acid Dissociable (WAD) cyanide determination includes the amount of cyanide species liberated at moderate pH of 4.5, for example HCN(aq) and $CN^-$. WAD cyanide determination accounts for the majority of Cu, Cd, Ni, Zn, Ag cyanide complexes and others compounds with similar low dissociation constants. That is, WAD cyanide determination is not limited to free cyanide only. As a result, and depending on the method used for determination, sample preparation for the determination of WAD cyanide can be significantly more complicated than that for free cyanide determination.

WAD cyanide analysis samples should be free from interferences due to the presence of high concentrations of more stable cyanide complexes or other cyanide forms. If not, the interference must be quantified and allowed for in the result. Thus, the automation of WAD cyanide analysis is less common.

It is not necessary to account for free cyanide in a WAD cyanide analysis, because WAD cyanide encompasses all free and weakly bound complexes. In fact, in the majority of the known techniques the measured WAD cyanide is derived from the amount or concentration of free cyanide in the sample.

Some automated WAD analysers have been developed using amperometric determination or colorimetric determination techniques. However, these methods have been known to exhibit inaccuracies of up to 25%. A more preferable determination method for the analysis of WAD cyanide is silver nitrate potentiometric titration due to the high level of accuracy that can be achieved. This is also the preferred method recommended by the International Cyanide Management Code developed for the gold mining industry. Unfortunately, this method of determination involves complicated sample pre-treatment, including distillation, which is not required for the colorimetric or amperometric techniques. Some other known automated on-line WAD cyanide analysers use techniques including the picric acid method of determination and ligand exchange.

A known laboratory method for measuring complex cyanide solutions involves distilling a 500 ml sample of a cyanide solution in a flask fitted with a thistle tube. During distillation HCN gas is liberated from the cyanide solution. Air is drawn through the thistle tube by suction, which causes the vapour and gasses from the flask to be drawn through a condenser attached to the flask. The gasses are then drawn through a caustic solution in an absorption tube where HCN gas liberated from the distillation step is then converted back to $CN^-$.

Using this method, any air and/or remaining gas drawn through the caustic solution is simply released to atmosphere. As such, the gas flow rate has to be very slow to ensure as much of the HCN gas as possible is absorbed by the caustic solution to minimise losses of HCN. The process takes approximately 1.5 hours, after which the absorption tube is removed and the sample taken away for analysis. Great care must also be taken to ensure all of the solution is removed from the tube prior to measurement to prevent losses and ensure an accurate quantitative measurement.

The flow rate must also be controlled for health and safety reasons. A slow flow rate may be required to ensure that all toxic HCN gas is absorbed in order to prevent the release of HCN gas.

Furthermore, cyanide samples tend to degrade over time and, although preservation techniques are available, it is preferable that any analysis be completed as soon as possible.

It is desired to address or ameliorate one or more disadvantages or shortcomings associated with existing chemical analysis apparatus and methods, and/or to at least provide a useful alternative thereto. The present invention seeks to reduce analysis times, losses of solution leading to inaccuracies and the requirement for manual handling of the sample before or during the analysis.

SUMMARY OF THE INVENTION

Certain embodiments of the present invention disclosed herein provide a method for determining the amount of cyanide in a sample and an apparatus suitable for use when performing such methods. However, the apparatus and method of the present invention are not specifically limited to the analysis of cyanide and may also be adapted to the analysis of other chemical species. Determining the amount of a chemical species includes, but is not limited to, determining the concentration of the chemical species in a sample.

In accordance with the present invention there is provided a method for determining the amount of a chemical species in a sample, said method comprising the steps of:
  i) treating the sample to liberate the chemical species into a gaseous stream;
  ii) directing the gaseous stream to a scrubber;
  iii) absorbing the chemical species into a scrubber solution; and
  iv) determining the amount of chemical species absorbed into the scrubber solution,
wherein any remaining chemical species not absorbed into the scrubber solution is directed or recirculated to the scrubber in the gaseous stream and step iii) is repeated to increase absorption of the chemical species prior to performing step iv).

In certain embodiments, step iii) is repeated to maximise absorption of the chemical species prior to performing step iv).

In accordance with the present invention there is further provided an apparatus for determining the amount of a chemical species in a sample, said apparatus comprising:
  i) a treatment unit for receiving the sample and liberating the chemical species into a gaseous stream;
  ii) a scrubber for receiving the gaseous stream from the treatment unit and absorbing the chemical species into a scrubber solution;
  iii) a recirculation conduit for directing or recirculating any chemical species not absorbed into the scrubber solution back to the scrubber in the gaseous stream to increase absorption of the chemical species; and
  iv) a measuring device for determining the amount of chemical species absorbed into the scrubber solution.

As noted above, the present invention is believed to be particularly suitable for use in cyanide analysis. Some embodiments are believed to be suitable for determining the amount of cyanide in the form of Weak Acid Dissociable ("WAD") cyanide. Alternatively, some embodiments may be suitable for determining the amount of cyanide in the form of total cyanide. Accordingly, another aspect of the present invention provides a method for measuring the amount of cyanide in a sample, said method comprising the steps of:
  i) treating the sample to liberate the cyanide as HCN gas into a gaseous stream;
  ii) directing the gaseous stream comprising the HCN gas to a caustic scrubber; iii) absorbing the cyanide into a caustic scrubber solution by converting it into $CN^-$; and
  iv) determining the amount of cyanide absorbed into the scrubber solution,
wherein any remaining cyanide not absorbed into the scrubber solution is directed or recirculated to the scrubber as HCN gas in the gaseous stream and step iii) is repeated to maximise absorption of the cyanide prior to performing step iv).

In accordance with the present invention there is still further provided an apparatus for determining the amount of cyanide in a sample, said apparatus comprising:
  i) a treatment unit for receiving the sample and liberating the cyanide as HCN gas into a gaseous stream;
  ii) a caustic scrubber for receiving the HCN gas from the treatment unit and absorbing the cyanide into a caustic scrubber solution by converting it to $CN^-$;
  iii) a recirculation conduit for directing or recirculating any cyanide not absorbed into the scrubber solution back to the scrubber as HCN gas in the gaseous stream to increase, and optionally maximise, absorption of the cyanide; and
  iv) a measuring device for determining the amount of cyanide absorbed into the scrubber solution.

BRIEF DESCRIPTION OF THE DRAWINGS

Various embodiments of the present invention will be described herein, by way of example only, with reference to the following drawings in which.

DETAILED DESCRIPTION OF THE INVENTION

The apparatus and method provided in certain embodiments may be useful for any system of chemical analysis that conventionally requires that a gaseous stream containing the desired chemical species is drawn through a chemical scrubber at a controlled rate to ensure complete absorption of the chemical species. In the present invention, the ability to recirculate the gaseous stream around the system multiple times is believed to overcome the requirement for a tightly controlled gas flow rate through the scrubber. In certain embodiments, the gas flow rate of the gaseous stream containing the desired chemical species is within the range of about 20 to 200 ml/min during recirculation. In some embodiments, the gaseous stream may be recirculated under positive pressure to improve gas flow and enhance absorption of the chemical species.

The sample is treated in the treatment unit to liberate the chemical species into a gaseous stream. The treatment may comprise a number of fluidly interconnected parts in which the sample may be progressively treated to liberate the chemical species. These parts include, but are not limited to, a mixing unit for mixing the sample and combining it with reagents, a heating unit, a distillation unit and a primary scrubber or filter for removing any undesirable species.

In some embodiments, the recirculation conduit may direct or recirculate the gaseous stream through one or more parts of the treatment unit, including any mixing unit, distillation unit, primary scrubber or filter. Accordingly, in some embodiments, parts of the treatment unit are interconnected using the recirculation conduit. A transfer pump may be used to pump the gaseous stream through the recirculation conduit.

The sample may be introduced to the treatment unit using a sample pump. In general, the sample is a solution comprising the chemical species. Often the solution is aqueous. The volume of the sample may be controlled by accurately metered peristaltic pumps fitted with optical sensors. In some embodiments the sample volume is measured by the sample pump. Embodiments of the apparatus may include a pump calibration feature to ensure a known volume of sample is added to the treatment unit. The sample volume may be within the range of from about 5 ml to about 250 ml, alternatively within a range of from about 5 ml to about 50 ml, alternatively within a range of from about 5 ml to about 20 ml, or alternatively within a range of from about 5 ml to about 10 ml. The appropriate sample volume may be selected based upon the approximate amount of chemical species and the known limitations of the technique used to determine the amount of chemical species in the sample. For example, in circumstances where it is known that the amount of chemical species is low, a larger sample volume may be required to conduct effective measurements.

The sample may be pumped through the treatment unit using a transfer pump. Transfer pumps may be used to pump both gas and liquids through the apparatus. Thus, in some embodiments, the same transfer pump is used to pump the sample solution through the treatment unit and to pump the gaseous stream containing the desired chemical species through the recirculation conduit.

In embodiments of the treatment unit comprising a mixing unit, the sample may be stirred and combined with one or more reagents in the mixing unit, as needed, to facilitate liberation of the chemical species into the gaseous stream. The amount of any reagent added to the mixing unit may be controlled using peristaltic pumps fitted with optical sensors, similar to those that may be used for the sample pump.

Depending upon the identity of the sample, a variety of reagents may be added to the mixing unit. For example, in the case of cyanide analysis a buffer may be added to bring a sample to the appropriate pH. The pH of the sample exiting the mixing unit may be buffered to within the range of about pH 4 and pH 5 for determination of the amount of WAD cyanide, optionally to within the range of about pH 4.5 and pH 5. Alternatively, the pH of the sample exiting the mixing unit may be buffered to pH<1 for total cyanide determination. To ensure that the sample is properly dosed with the reagents, the mixing unit may have a pH meter fitted.

In practice, suitable reagents and the optimum amounts to be used may be determined experimentally. The following provides a general description of reagents that are likely to be of use, particularly in relation to cyanide analysis. However, it is envisaged that the apparatus and method of the present invention is not specifically limited to the analysis of cyanide and may also be adapted to the analysis of other chemical species.

Suitable reagents for cyanide analysis include, but are not limited to, an acetate buffer and/or zinc acetate solution for buffering the sample to the correct pH for, for example, determination of the amount of cyanide in the form of WAD cyanide. In some circumstances, the sample may be too alkaline to buffer, and it may be necessary to add acid to correct the sample pH. The addition of acid to a sample may be necessary when the total cyanide concentration of a sample is being determined, in order to adjust the pH to an appropriate level. In some embodiments, a sample may be analysed at a pH within the range suitable for WAD cyanide determination. Then, a sample may be acidified and analysed to determine total cyanide concentration. Accordingly, it is possible to take a series of measurements using the apparatus of the present invention. In some embodiments, the apparatus will comprise a buffer pump to add buffer to a sample to achieve a certain pH, and a reagent pump to add an acid or another reagent.

In some embodiments, after buffering or the addition of other reagents, samples of the solution or mixture in the mixing unit may be collected using another sample pump for quality control analysis.

Once any reagents have been combined with the sample, the sample may be transferred from the mixing unit to another part of the treatment unit in order to further treat the sample and liberate the chemical species. In some embodiments, the sample may be heated in a heating unit to liberate the chemical species into the gaseous stream. Alternatively or additionally, the sample may be transferred to a distillation unit wherein the sample is distilled to liberate the chemical species. Distilling or heating may convert the chemical species into a gas containing the chemical species. In the aspects of the present invention related to cyanide analysis, the cyanide may be converted to HCN gas in the distillation unit. The HCN gas is then liberated into the gaseous stream.

It is envisaged that the continuous recirculation of the gaseous stream through the apparatus during the process of liberating the chemical species ensures that any chemical species not absorbed on the first pass through the scrubber is returned back to the scrubber through a recirculation conduit and the absorption process is repeated. Thus, maximum absorption of the chemical species into the chemical scrubber solution does not have to be achieved on the first pass. In some embodiments, recirculation of the gaseous stream through the recirculation conduit is performed using the transfer pump. The gas flow rate in certain embodiments may be higher than prior art methods. Furthermore, in some embodiments, including some in which the chemical species is cyanide, the gaseous stream may be continuously recirculated distillation. Thus, as a result of the higher gas flow rate, for those embodiments the distillation time may be significantly reduced. The total distillation time may be within the range of from about 5 to 30 minutes, optionally within the range of from about 5 to 15 minutes.

The distillation unit may comprise a lower chamber for heating the sample, and an upper chamber, for condensing any vapour produced. The lower chamber is preferably provided in the form of an acid and heat resistant tube which passes through a heating block. Due to the small volumes involved in some embodiments, the solution may be heated to a rapid boil in a relatively short space of time.

The upper chamber preferably comprises a valve for venting, used when filling and/or draining the system. Generally, the valve remains closed during the distillation process so that the apparatus forms a closed system.

In some embodiments, the lower chamber is coupled to the upper chamber via an insulating chamber having a larger diameter with respect to the lower and upper chambers.

Upon exiting the upper chamber, the gaseous stream carrying the chemical species may then pass through a primary scrubber and/or filter to remove undesirable species or contaminants. For example, sulphides may be removed from the gaseous stream during cyanide analysis as they can interfere with the final cyanide measurement. The primary scrubber may comprise a tube filled with a primary scrubber solution through which the gas is passed. In embodiments in which it is desired to remove sulphides, the primary scrubber solution may comprise lead acetate. Alternatively, the primary scrubber may comprise a resin or any other material capable of absorbing the undesirable species without removing the desired chemical species from the gaseous stream.

After passing through any primary scrubber or filter, the gaseous stream is then transferred to the scrubber. The gaseous stream that exits the scrubber is recirculated using the recirculation conduit. In some embodiments, the gaseous stream is recirculated continuously through the apparatus during the liberation of the chemical species into the gaseous stream. The gaseous stream may be recirculated under positive pressure to facilitate and enhance the flow of gas through the system and absorption of the chemical species.

The scrubber contains a solution to absorb the desired chemical species in the gaseous stream. The chemical species may be absorbed into the scrubber solution by converting it into a different chemical form. The amount of chemical species measured in the scrubber solution is related back to the amount of chemical species in the original sample volume.

In the embodiments related to measurement of the concentration of WAD and/or total cyanide, the scrubber may be a caustic scrubber in which there is a caustic solution comprising sodium hydroxide. The cyanide liberated into the gaseous stream as HCN gas may be passed into the scrubber and absorbed by converting the cyanide back to $CN^-$ in the caustic scrubber solution. The amount of $CN^-$ in the scrubber solution may be related back to the concentration of cyanide (in ppm) in the original sample.

The concentration of sodium hydroxide in the caustic scrubber may be within the range of about 20 to about 50 g/L. The pH of the caustic solution within the caustic scrubber is at least about pH 11.5, in some embodiments.

The apparatus further comprises a measuring device or cell for determining the amount of cyanide absorbed into the scrubber solution. In certain embodiments, the measuring device is a potentiometric cell. For cyanide analysis, a particularly suitable measuring device is an automatic titrator that dispenses a potentiometric silver nitrate titration. However, other methods for measurement, such as colorimetric, amperometric or ion-selective electrode techniques, may also be employed.

The scrubber may be combined with the measuring device. Thus, in some embodiments, the measuring device is in contact with the scrubber solution in the scrubber such that the amount of chemical species is determined in situ. By combining the measuring device and the scrubber and/or performing measurements directly within the scrubber, the need to transfer the scrubber solution to another receptacle is overcome. Thus, inaccuracies in measurement that may result from losses of the scrubber solution, and the absorbed cyanide, during the transfer of solution may be ameliorated or substantially obviated.

It is contemplated that, in some embodiments, the apparatus is controlled through the use of operating software. It is further contemplated that through modification of the operating conditions it would be possible to measure either WAD, total or free cyanide. As described above, WAD cyanide analysis is performed by distillation of the sample at a buffered pH. Total cyanide may be measured in the same way, but the sample should be strongly acidified through the addition of a reagent to the mixing unit. Certain embodiments of the apparatus may also be used to measure the free cyanide concentration of samples by pumping the sample directly into the measuring cell or distilling the sample without the addition of any reagents.

The mixing unit, primary scrubber, scrubber and measurement device may undergo a, preferably automatic, rinse after each measurement. In some embodiments, rinsing may be performed by reversing the transfer pump and taking the sample residue back into the mixing unit, which may be fitted with an electro-mechanical drain. The sample residue in the mixing unit and the scrubber solution, which may be in the scrubber and/or the measuring device, are drained to waste. After draining, the mixing unit, the scrubber and the measuring device are rinsed with clean water. With the transfer pump still running in reverse, clean water is drawn from the measuring device and/or the scrubber to the mixing unit via the distillation unit, so that the distillation unit is also rinsed. Periodically, the system may be automatically rinsed with a specific cleaning solution to prevent any scale build up.

Certain embodiments of the apparatus have been designed to be fully on-line automatic instruments, but, if required, embodiments could also be operated in a lab, either semi-automatically or manually. In some embodiments, the apparatus is contained within a receptacle.

Where embodiments of the apparatus are used inline in a chemical process, for example a mineral processing plant, the apparatus preferably comprises one or more sample filters to facilitate separation of solids from the sample prior to introducing the sample into the treatment unit. In some embodiments the samples are introduced using a sample pump. In some embodiments, the apparatus has one or more in-built filtration pumps that draw a clear filtrate from the sample point to one or more sample reservoirs within the analyser apparatus. The filtered sample solution may be stored in a reservoir located within the apparatus to enable sampling via the sample pump at a later time.

In some embodiments the filter comprises a sintered filter element, for example, a sintered stainless steel pipe, or a plastic perforated pipe with a filter cloth cover. The sample filter may include a back-flush mechanism to substantially remove solids build-up on the filter element. This may be desirable when a sintered element is used.

The filter may be joined to the tube connecting it with the apparatus with a filter adaptor. In some embodiments, the filter adaptor will have two tubes running through it: one to take the filtrate away and the other to blow compressed air into the filter to remove cake build-up from the surface of the filter. Embodiments of the apparatus may comprise a solenoid to control the rate and amount of the air blown back.

Depending upon the end use of the apparatus, samples may be collected from a leach tank, effluent stream or effluent pond using the apparatus. It is envisaged that some embodiments of the apparatus of the present invention can be fitted inline with a mineral processing plant to provide automated real-time analysis. In certain embodiments, the real time analysis is conducted by performing batch testing at regular intervals.

Figure 1:
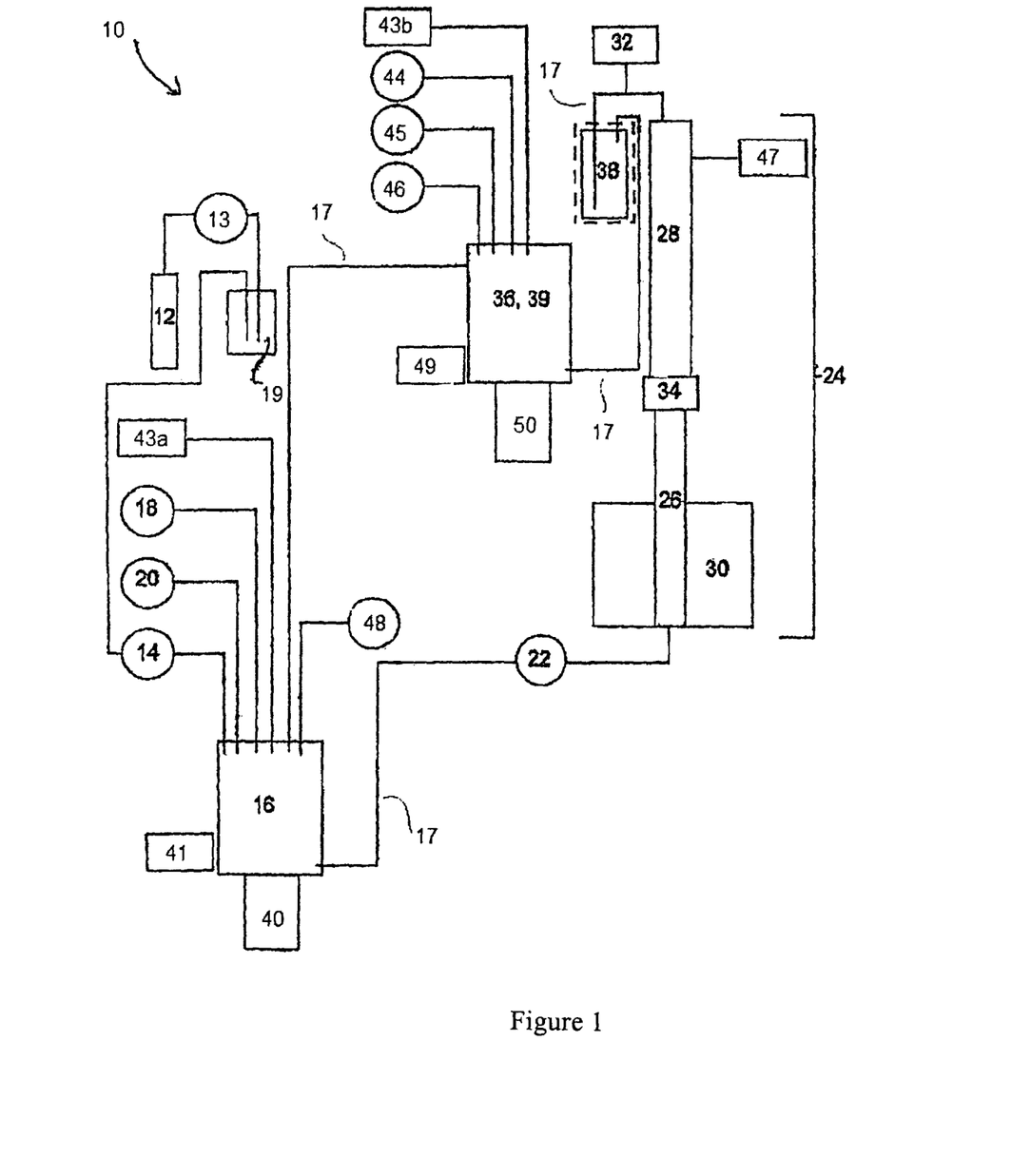
FIG. 1 is a diagrammatic representation of an apparatus for the automated measurement of the concentration of WAD and/or total cyanide in accordance with the present invention.

The present invention will be further described, by way of non-limiting example only, with reference to the following embodiments illustrated by FIG. 1. However, it is to be understood that the particularity of the following description is not to supersede the generality of the preceding description of the invention.

In FIG. 1 there is shown a block diagram illustrating an embodiment of an apparatus 10 and method for the measurement of WAD cyanide in solution in accordance with the present invention.

The apparatus 10 comprises a sample filter 12 to filter the cyanide sample solution as it is drawn into the apparatus by a filter pump 13. After filtering, the sample is transferred to a reservoir 19 by the filter pump 13. The filtered sample may be stored in the reservoir 19 to enable sampling at a later time. The volume of the sample may be within the range of 5 to 50 ml, for example 5 to 10 ml. The cyanide sample solution is sampled by a sample pump 14 and accurately dosed into a mixing unit 16 in which reagents, for example, an acid, are added by a reagent pump 18. After transfer to the mixing unit 16 the pH is adjusted to the desired value of between pH 4.5 and pH 5, for example between pH 4.5 and pH 4.7, for determination of the amount of cyanide in the form of WAD cyanide. The pH is adjusted using a buffer solution, for example an acetate buffer and/or zinc acetate solution, dosed to the mixing unit via a buffer pump 20. During the addition of the buffer solution or any other reagent the sample is stirred using a stirrer 40. To ensure that the solution is properly dosed with the buffer solution, the mixing unit 16 may have a pH meter fitted. In some embodiments, it may be useful to take samples of the buffer solution for, for example, quality control analysis, using a sample pump 48.

A transfer pump 22 directs the buffered sample through a recirculation conduit 17 to a distillation unit 24. The transfer pump 22 may be operated throughout the process to transfer liquid and gas through the system via the recirculation conduit 17. As any gas in the apparatus may be continuously recirculated, the requirement to utilise a tightly controlled gas flow rate is overcome. In some embodiments, the transfer pump 22 can provide positive air pressure within the system in order to facilitate the flow of gas through the system and absorption of the chemical species.

The distillation unit 24 has a lower chamber 26 and an upper chamber 28. The lower chamber 26 may be in the form of an acid and heat resistant tube which passes through a heating block 30 and is where the sample is brought to a rapid boil. Due to the small volumes involved, the sample can be heated to a rapid boil in a minimal amount of time. The total distillation time may be reduced to within 5 to 30 minutes, for example, 5 to 15 minutes. The upper chamber 28, also known as a cooling chamber or condenser, may be fitted with a valve 32 for venting the system and allowing the distillation unit 24 to be filled and drained. The valve 32 remains closed during distillation. An insulating chamber 34 is situated between the lower chamber 26 and upper chamber 28. The insulating chamber 34 has a larger diameter to assist any refluxed liquid to return to the lower chamber for re-boiling and prevents liquid from passing through the top of the upper chamber 28 and ultimately entering a measuring cell 36 in the form of a potentiometric cell, for example. Cooling water may be used to cool the upper chamber 28, so that it condenses the sample vapour effectively. The cooling water is introduced into the apparatus 10 using cooling water solenoid 47.

During the distillation process HCN gas is liberated from the sample solution and is carried by the flow of the gaseous stream, including air, provided by the transfer pump 22. The combined air and HCN gas stream exits the top of the upper chamber 28 and proceeds through the recirculation conduit 17 to a primary scrubber 38 containing, for example, lead acetate to remove undesirable species, for example sulphides, which can interfere with the final measurement of concentration. The primary scrubber 38 may be in the form of tube.

The combined air and HCN gas stream may then be bubbled through a caustic solution, for example sodium hydroxide solution, contained in a scrubber 39 and having a pH of at least pH 11.5 and a sodium hydroxide concentration within the range of 20 to 50 g/L. In this instance the measuring cell 36 also doubles as the scrubber 39, although it is to be understood that they may be provided as separate units. This reduces solution handling requirements and therefore reduces the likelihood of losses as a result of transferring the caustic solution (containing absorbed cyanide) into a separate measuring cell.

As the combined air and HCN gas stream passes through the caustic scrubber solution, HCN gas is absorbed into the solution to form $CN^-$. Due to the fact that the apparatus forms a closed system, any HCN gas carried by the air stream that is not absorbed by the solution exits the top of the scrubber 39 and is recirculated back through the system via the transfer pump 22 and distillation unit 24 using the recirculation conduit 17. This recirculated gaseous stream is thus ultimately passed again through the scrubber 39 to maximise the absorption of HCN from the combined air and gas stream. As a result, the flow rates can be faster and distillation times significantly reduced when compared to known methods in which the combined air and gas stream can only be passed through the scrubber a single time. The flow rate of the combined air and gas stream through the apparatus 10 may be within the range of 20 to 200 ml/min.

The length of the distillation process may be significantly reduced as a result of the higher gas flow rates. Distillation times of between 5 to 30 minutes (based on a sample size of between 5 and 10 ml) will generally ensure that the combined air and gas stream is passed through the caustic solution a sufficient number of times to ensure that substantially all of the HCN gas converted to $CN^-$ and absorbed into the scrubber solution.

Once the distillation process is complete, the concentration of cyanide in the caustic scrubber solution can be determined by a silver nitrate potentiometric titration which is conducted directly within the measuring cell 36. However, other measurement methods may be employed, for example amperometric, colorimetric or ion selective electrode. By combining the measuring cell 36 and the scrubber 39 and/or performing the measurement directly within the measuring cell 36, the need to transfer the solution to another cell is overcome and inaccuracies in the measurement as a result of losses of cyanide during the transfer of solution may be ameliorated or substantially obviated. In the illustrated embodiment the silver nitrate solution is introduced into the measuring cell 36 using a silver pump 45 and combined with the scrubber solution using a stirrer 50.

Following determination of the amount of cyanide in the scrubber solution the amount of amount of cyanide in the sample can be determined based upon the amount measured in the scrubber solution and the original size, for example volume, of the sample.

After each measurement cycle, the mixing unit 16, scrubber 39 and measuring cell 36 may undergo an automatic rinse. The primary scrubber 38, if present, may also be drained and rinsed in a similar fashion to the measuring cell 36 and the mixing unit 16, every measurement cycle.

Rinsing may be performed by reversing the transfer pump 22 and taking the residual solution back into the mixing unit 16, which is fitted with an electro-mechanical drain, operated using a drain solenoid 41. The residual solution in the mixing unit 16, the scrubber 39 and the measuring cell 36 are drained to waste. In the illustrated embodiment, the scrubber 39 and the measuring cell 36 are combined and may be drained by operating an electro-mechanical drain using a drain solenoid 49. After draining, both the mixing unit 16 and the measuring cell 36 are rinsed with clean water. The water is introduced into the apparatus via a rinse inlets operated by rinse solenoids 43a and 43b. With the transfer pump 22 continuing to run in reverse, clean water is drawn from the measuring cell 36 to the mixing unit 16 via the distillation unit 24, so that the distillation unit 24 is also rinsed. Periodically, the system may be automatically rinsed with a specific cleaning solution using cleaning pump 46 to prevent any scale build up.

Following rinsing, the chemical scrubber is refilled with the caustic solution using a caustic pump 44.

The invention is now illustrated further by, but is in no way limited to, the following examples. Throughout the examples, E=potential, measured in mV, V=Volume of silver nitrate solution (ml), D=Delta (DE/DV).

Example 1

Figure 2:
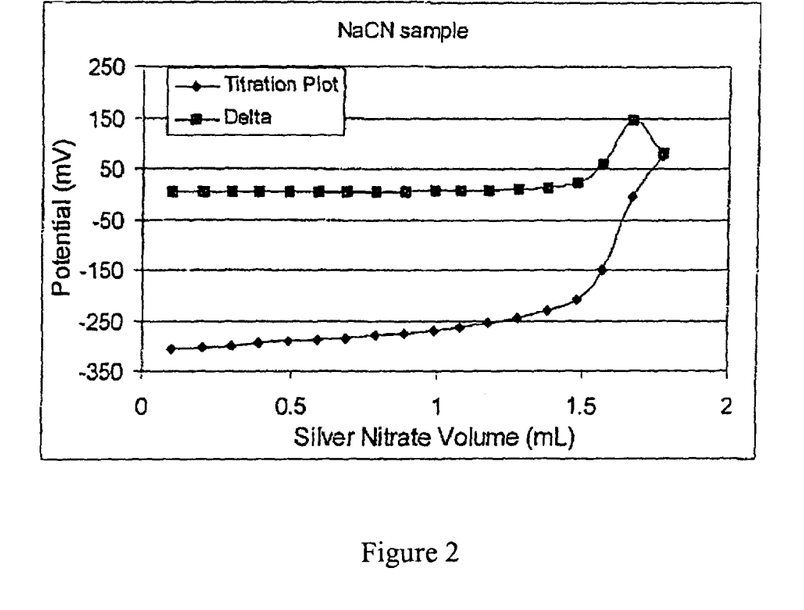
FIG. 2 is a graphical representation of a silver nitrate potentiometric titration of a cyanide sample in Example 1, with no pre-treatment, containing approximately 80 ppm NaCN (~42.5 ppm $CN^-$)
Figure 3:
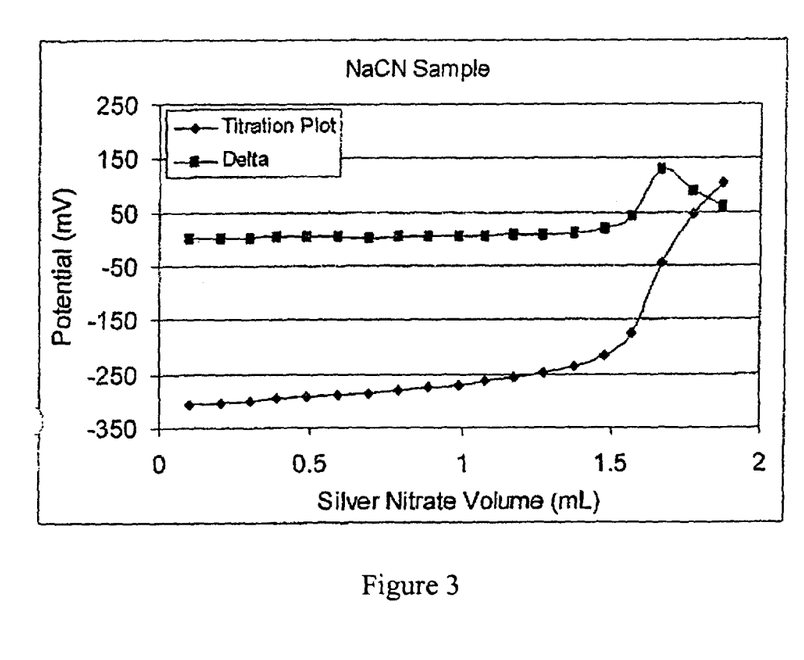
FIG. 3 is a graphical representation of the results obtained in Example 1 by running a sample through an apparatus of the present invention.

FIGS. 2 and 3 show the recovery of cyanide from a 5 ml sample treated by an apparatus of the present invention, and the concentration measured. These experiments were carried out using sodium cyanide samples, with no complexing metals present. For each sample the distillation time was 5 minutes and the result yielded was 43 ppm indicating 100% recovery. The same sample was put through the apparatus five times over a one-hour period and produced a result of 43 ppm for each measurement. These results are typical and are consistent through a range of different cyanide concentrations.

Table 1 shows the measurements of a potentiometric titration using a silver nitrate solution, with no pre-treatment, on a sample containing approximately 80 ppm NaCN (~42.5 ppm $CN^-$). This is represented graphically in FIG. 2. The sample was measured by a potentiometric titration and yielded a result of 43 ppm.

TABLE 1

| Titration without distillation | | |
|---|---|---|
| E (mV) | V (ml) | D (DE/DV) |
| −306 | 0.10 | 3 |
| −303 | 0.20 | 3 |

TABLE 1-continued

| Titration without distillation | | |
|---|---|---|
| E (mV) | V (ml) | D (DE/DV) |
| −300 | 0.30 | 3 |
| −296 | 0.39 | 4 |
| −293 | 0.49 | 3 |
| −289 | 0.59 | 4 |
| −285 | 0.69 | 4 |
| −280 | 0.79 | 5 |
| −275 | 0.89 | 5 |
| −269 | 0.99 | 6 |
| −263 | 1.08 | 6 |
| −255 | 1.18 | 8 |
| −245 | 1.28 | 10 |
| −231 | 1.38 | 14 |
| −208 | 1.48 | 23 |
| −149 | 1.57 | 59 |
| −5 | 1.67 | 144 |
| 76 | 1.77 | 81 |

S1 = 43 ppm

A sample from the same solution was put through the apparatus, and distilled at pH 4.5 and the result is depicted in Table 2 and FIG. 3.

TABLE 2

| E (mV) | V (ml) | D (DE/DV) |
|---|---|---|
| −306 | 0.10 | 3 |
| −303 | 0.20 | 3 |
| −300 | 0.30 | 3 |
| −296 | 0.39 | 4 |
| −292 | 0.49 | 4 |
| −288 | 0.59 | 4 |
| −285 | 0.69 | 3 |
| −280 | 0.79 | 5 |
| −275 | 0.89 | 5 |
| −270 | 0.99 | 5 |
| −264 | 1.08 | 6 |
| −257 | 1.18 | 7 |
| −248 | 1.28 | 9 |
| −236 | 1.38 | 12 |
| −217 | 1.48 | 19 |
| −175 | 1.57 | 42 |
| −45 | 1.67 | 130 |
| 45 | 1.77 | 90 |
| 105 | 1.87 | 60 |

S1 = 43 ppm

During this experiment, the apparatus was able to produce excellent recoveries with very short distillation times.

Example 2

Figure 4:
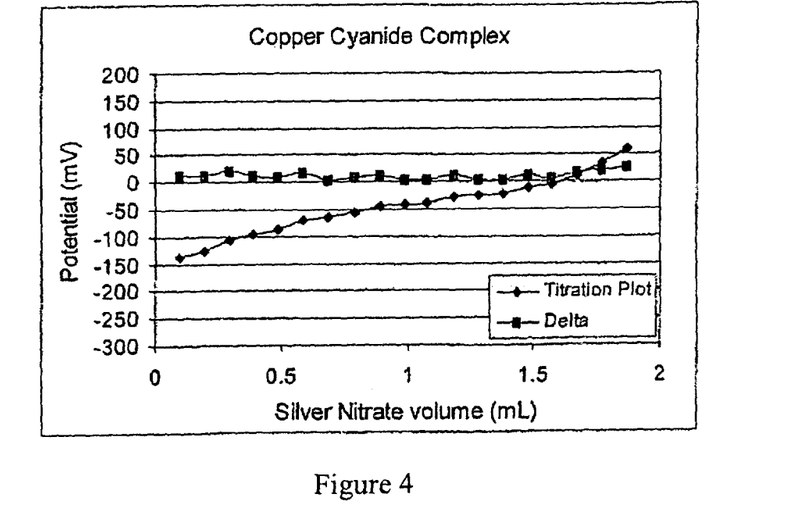
FIG. 4 is a graphical representation of a silver nitrate potentiometric titration of a WAD cyanide sample in Example 2 made from NaCN complexed with copper.
Figure 5:
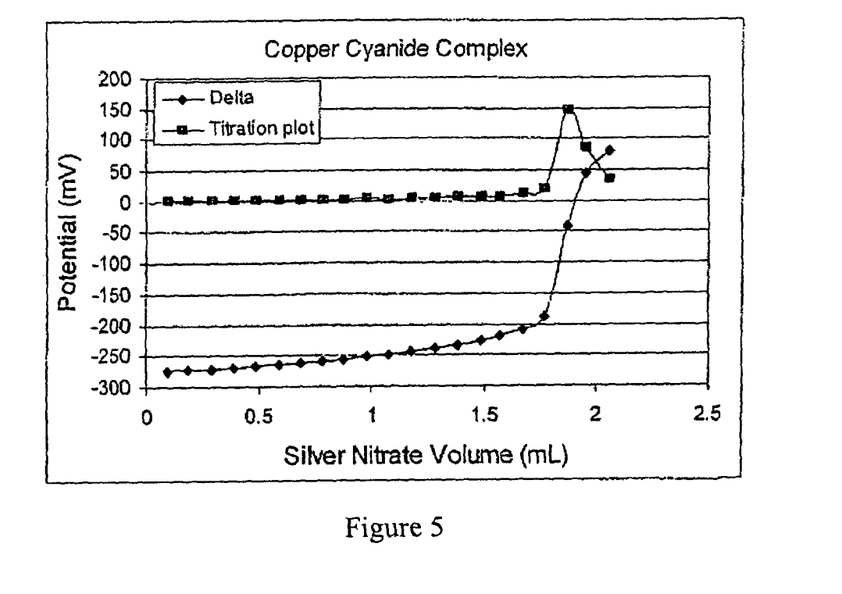
FIG. 5 is a graphical representation of the results obtained in Example 2 by running a sample through an apparatus of the present invention.

FIGS. 4 and 5 show the results of testing samples of WAD cyanide made from NaCN complexed with copper. The samples were tested in the same manner as those of Example 1.

Table 3 below shows measurements from the sample titrated without any pre-treatment. This titration is shown graphically in FIG. 4. As the end-point could not be reasonably determined potentiometrically by a differential potential (Delta), the endpoint was selected by a default potential that was determined colorimetrically by the addition of rhodanine to the cell. This yielded a result of 9 ppm.

TABLE 3

| E (mV) | V (ml) | D (DE/DV) |
|---|---|---|
| −138 | 0.10 | 11 |
| −126 | 0.20 | 12 |

TABLE 3-continued

| E (mV) | V (ml) | D (DE/DV) |
|---|---|---|
| −107 | 0.30 | 19 |
| −95 | 0.39 | 12 |
| −86 | 0.49 | 9 |
| −69 | 0.59 | 17 |
| −65 | 0.69 | 4 |
| −57 | 0.79 | 8 |
| −44 | 0.89 | 13 |
| −41 | 0.99 | 3 |
| −38 | 1.08 | 3 |
| −27 | 1.18 | 11 |
| −24 | 1.28 | 3 |
| −22 | 1.38 | 2 |
| −10 | 1.48 | 12 |
| −4 | 1.57 | 6 |
| 13 | 1.67 | 17 |
| 34 | 1.77 | 21 |
| 59 | 1.87 | 25 |

S1 = 9 ppm

A sample of the same solution was then put through a WAD cyanide analyser apparatus in accordance with the present invention and the amount of cyanide was measured. The distillation time was only five minutes. The measurements are shown in Table 4. A graph of the titration used to measure the amount of cyanide is shown in FIG. 5. This time the result was 48 ppm and the endpoint was very well defined.

TABLE 4

| E (mV) | V (ml) | D (DE/DV) |
|---|---|---|
| −275 | 0.10 | 2 |
| −273 | 0.19 | 2 |
| −271 | 0.29 | 2 |
| −270 | 0.39 | 1 |
| −267 | 0.49 | 3 |
| −265 | 0.59 | 2 |
| −263 | 0.69 | 2 |
| −260 | 0.79 | 3 |
| −257 | 0.88 | 3 |
| −253 | 0.98 | 4 |
| −250 | 1.08 | 3 |
| −245 | 1.18 | 5 |
| −240 | 1.28 | 5 |
| −234 | 1.38 | 6 |
| −227 | 1.48 | 7 |
| −219 | 1.57 | 8 |
| −208 | 1.67 | 11 |
| −188 | 1.77 | 20 |
| −41 | 1.87 | 147 |
| 46 | 1.96 | 87 |
| 81 | 2.06 | 35 |

S1 = 48 ppm

Embodiments have been described herein with reference to the figures and examples. However, some modifications to the described embodiments and/or examples may be made without departing from the spirit and scope of the described embodiments, as described in the appended claims.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout the specification and claims, unless the context requires otherwise, the word "comprise" or variations such as "comprises" or "comprising", will be understood to imply the inclusion of a stated integer or group of integers but not the exclusion of any other integer or group of integers.

Throughout the specification, unless the context requires otherwise, the work "automated" or "automatic", will be understood to imply machine automated.

The invention claimed is:

1. A method for determining the amount of a chemical species in a known volume of sample solution, said method comprising the steps of:
   i) treating the known volume of sample solution to liberate the chemical species into a gaseous stream within a closed system;
   ii) directing the gaseous stream under positive pressure to a scrubber within the closed system;
   iii) absorbing the chemical species into a scrubber solution; and
   iv) determining the amount of chemical species absorbed into the scrubber solution, wherein any remaining chemical species not absorbed into the scrubber solution is directed or recirculated within the closed system under positive pressure to the scrubber in the gaseous stream and step iii) is repeated to increase absorption of the chemical species prior to performing step iv).

2. The method according to claim 1, wherein step iii) is repeated to an extent sufficient to maximise absorption of the chemical species prior to performing step iv).

3. The method according to claim 1, wherein treating the known volume of sample solution comprises mixing the known volume of sample solution with one or more reagents to facilitate liberation of the chemical species into the gaseous stream.

4. The method according to claim 3, wherein the mixing results in adjustment or control of the pH of the sample.

5. The method according to claim 4, wherein the chemical species is cyanide.

6. The method according to claim 5, wherein the cyanide is in the form of Weak Acid Dissociable ("WAD") cyanide.

7. The method according to claim 6, wherein the mixed sample has a pH of from about pH 4 to about pH 5.

8. The method according to claim 5, wherein the cyanide is in the form of total cyanide.

9. The method according to claim 8, wherein the mixed sample has a pH<1.

10. The method according to claim 5, wherein treating the known volume of sample solution comprises distilling the known volume of sample solution to liberate the cyanide into the gaseous stream.

11. The method according to claim 10, wherein the gaseous stream is recirculated continuously during distillation.

12. The method according to claim 10, wherein distillation converts the cyanide into HCN gas.

13. The method according to claim 12, wherein the HCN gas is absorbed into the scrubber solution by converting it to CN.

14. The method according to claim 1, wherein treating the known volume of sample solution comprises heating the sample to liberate the chemical species into the gaseous stream.

15. The method according to claim 1, wherein the scrubber solution comprises sodium hydroxide.

16. The method according to claim 1, wherein determining the amount of chemical species absorbed into the scrubber solution comprises performing a titration using the scrubber solution.

17. The method according to claim 1, wherein the gaseous stream is directed at a flow rate of from about 20 to 200 ml/min.

18. An apparatus for determining the amount of cyanide in a known volume of sample solution, said apparatus comprising:
   i) a treatment unit for receiving the known volume of sample solution and liberating the cyanide into a gaseous stream within a closed system;
   ii) a scrubber containing a cyanide absorbing scrubber solution for receiving the gaseous stream from the treatment unit and absorbing the cyanide into the cyanide absorbing scrubber solution within the closed system;
   iii) a recirculation conduit for directing or recirculating within the closed system under positive pressure any cyanide not absorbed into the cyanide absorbing scrubber solution back to the scrubber in the gaseous stream to increase absorption of the cyanide;
   iv) a measuring device for determining the amount of cyanide absorbed into the cyanide absorbing scrubber solution; and
   v) a transfer pump for pumping the gaseous stream through the recirculation conduit.

19. An apparatus for determining the amount of a chemical species in a known volume of sample solution, said apparatus comprising:
   i) a treatment unit for receiving the known volume of sample solution and liberating the chemical species into a gaseous stream within a closed system;
   ii) a scrubber for receiving the gaseous stream from the treatment unit and absorbing the chemical species into a scrubber solution within the closed system;
   iii) a recirculation conduit for directing or recirculating within the closed system under positive pressure any chemical species not absorbed into the scrubber solution back to the scrubber in the gaseous stream to increase absorption of the chemical species;
   iv) a measuring device for determining the amount of chemical species absorbed into the scrubber solution; and
   v) a transfer pump for pumping the gaseous stream through the recirculation conduit.

20. The apparatus according to claim 19, wherein the treatment unit comprises a mixing unit for mixing the known volume of sample solution with one or more reagents to facilitate liberation of the chemical species into the gaseous stream.

21. The apparatus according to claim 19, wherein the treatment unit comprises a heating unit for heating the known volume of sample solution to liberate the chemical species into the gaseous stream.

22. The apparatus according to claim 19, wherein the treatment unit comprises a distillation unit for distilling the known volume of sample solution to liberate the chemical species into the gaseous stream.

23. The apparatus according to claim 19, wherein the scrubber solution comprises sodium hydroxide.

24. The apparatus according to claim 19, wherein the measuring device is in contact with the scrubber solution in the scrubber such that the amount of chemical species is determined in situ.

25. The apparatus according to claim 19, wherein the recirculation conduit directs or recirculates any chemical species not absorbed into the scrubber solution back to the scrubber in the gaseous stream through at least one part of the treatment unit.

26. The apparatus according to claim 19, wherein the scrubber, the treatment unit, and the transfer pump are interconnected by the recirculation conduit, such that the transfer pump acts to pump the known volume of sample solution through the treatment unit to the scrubber and further acts to pump any chemical species not absorbed into the scrubber solution through the treatment unit back to the scrubber.

* * * * *

UNITED STATES PATENT AND TRADEMARK OFFICE
CERTIFICATE OF CORRECTION

PATENT NO.       : 8,513,022 B2                                             Page 1 of 1
APPLICATION NO. : 12/808634
DATED            : August 20, 2013
INVENTOR(S)      : Fraser John Ross It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this

Fifteenth Day of September, 2015

Michelle K. Lee
*Director of the United States Patent and Trademark Office*